United States Patent [19]

Songer et al.

[11] Patent Number: 4,892,519
[45] Date of Patent: Jan. 9, 1990

[54] STEERABLE PERFUSION DILATATION CATHETER

[75] Inventors: Ronald W. Songer; Peter R. McInnes, both of Sunnyvale, Calif.

[73] Assignee: Advanced Cardiovascular Systems, Inc., Mountain View, Calif.

[21] Appl. No.: 128,154

[22] Filed: Dec. 3, 1987

[51] Int. Cl.⁴ .................................. A61M 25/00
[52] U.S. Cl. .......................... 604/96; 606/194; 606/159
[58] Field of Search .................. 128/344, 368.1; 604/96–103

[56] References Cited

U.S. PATENT DOCUMENTS 4,616,653 10/1986 Samson et al. ................ 604/344
4,744,366 5/1988 Jang ............................ 604/344

Primary Examiner—Dalton L. Truluck
Attorney, Agent, or Firm—Fulwider, Patton, Lee & Utecht

[57] ABSTRACT

A steerable dilatation catheter with perfusion holes for use in coronary angioplasty. The catheter has inner and outer tubular members, with an inflatable balloon near the distal end of the outer tubular member. The guidewire extends through a lumen in the inner tubular member, and the distal end portions of the tubular members are sealed to the guidewire to close the distal end of this passageway. An annular lumen is formed between the inner and outer tubular members for the passage of inflating fluid to the interior of the balloon. The sidewalls of the tubular members are sealed together completely around the inner periphery of the distal ends thereof and over a limited area proximal to the balloon. Perfusion holes extend through the sealed sidewalls of the tubular members on both the proximal and distal of the balloon.

5 Claims, 1 Drawing Sheet

STEERABLE PERFUSION DILATATION CATHETER

BACKGROUND OF THE INVENTION

This invention generally relates to perfusion catheters and more particularly to steerable perfusion dilatation catheters for use in coronary angioplasty.

In percutaneous transluminal coronary angioplasty, catheters are inserted into the cardiovascular system through the femoral or brachial arteries under local anesthesia. A preshaped guiding catheter is positioned in the coronary artery, and a dilatation catheter having a distensible balloon portion is advanced through this catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery.

A guidewire is often employed to facilitate placement of the dilatation catheter beyond the distal end of the guiding catheter The guidewire is inserted through the guiding catheter, and the dilatation catheter is advanced along the guidewire to the desired position in the vascular system.

Since the inflated balloon occludes the flow of blood in the artery or other vessel being treated, the balloon can only be inflated for a limited time, typically on the order of 15–60 seconds. A longer inflation time would be desirable since it would increase the probability that the vessel would remain open after the catheter is removed. With catheters heretofore provided, however, the only way to prolong the inflation is to use repeated short inflations.

Attempts have been made to provide blood flow around the inflated balloon of a dilation catheter during a coronary angioplasty procedure. Examples of these prior art techniques are found in U.S. Pat. Nos. 4,423,725 (Baran et al.) and 4,581,017 (Sahota) and in Ser. No. 903,028, filed Sept. 2, 1986, assigned to the present assignee. Reference is also made to U.S. Pat. No. 4,661,094 also assigned to the present assignee, which discloses a perfusion catheter which does not have an inflatable balloon but does have holes and a flow passage for carrying blood through an obstruction in a blood vessel. The aforesaid references are hereby incorporated herein in their entirety. However, what has been needed and has been heretofore unavailable are steerable dilatation catheters having means to facilitate the flow of blood when the balloon is inflated. The present invention satisfies this need.

SUMMARY OF THE INVENTION

The present invention provides an improved dilatation catheter which is steerable and provides for blood flow distally to the inflated balloon.

The steerable dilatation catheter in accordance with the invention comprises inner and outer tubular members, with the outer tubular member having an inflatable balloon toward its distal end and an annular passageway formed between the tubular members for inflation and deflation of the balloon. A guidewire extends through the lumen of the inner tubular member. The tubular members are sealed together on the distal side of the balloon and in a limited area on the proximal side thereof. Perfusion openings are formed in the side walls of the tubular members where they are formed in the sidewalls of the tubular balloon to facilitate blood flow through the lumen of the inner tubular member. One or more openings distal to the balloon are provided to discharge blood from the lumen of the inner member. Preferably, the distal end portion of the inner or outer tubular member or both are sealed to the guidewire on the distal side of the balloon. The catheter of the invention can be readily steered to the desired location as described in U.S. Pat. No. 4,582,181, assigned to the present assignee, which is incorporated herein in its entirety by reference thereto.

These and other advantages of the invention will become more apparent from the following detailed discussion thereof and the accompanying exemplary drawings.

DETAILED DESCRIPTION OF THE INVENTION

Figure 1:
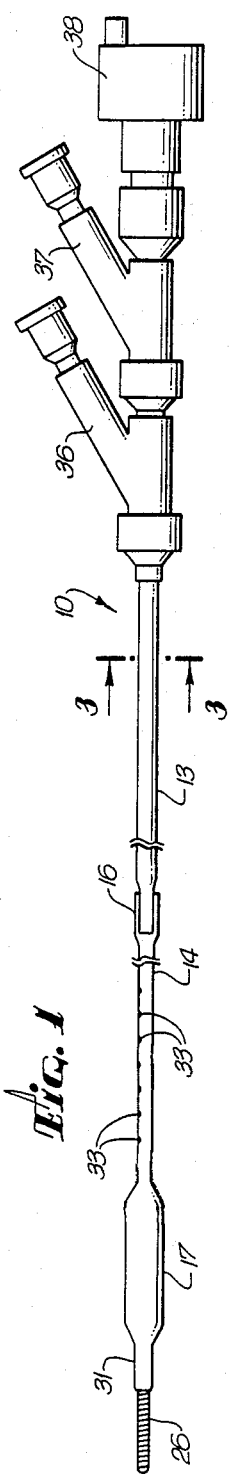
FIG. 1 is a side elevational view of one embodiment of a steerable perfusion dilatation catheter embodying features of the invention.

As illustrated in the drawings, the catheter 10, which embodies features of the invention, includes an inner tubular member 11 and an outer tubular member 12, with the inner tubular member being positioned within the outer tubular member throughout substantially the entire length of the catheter. The outer tubular member has a proximal section 13 and a distal section 14 which are joined together as indicated at 16 by suitable means, such as heat sealing or adhesive bonding. The two sections permit different portions of the outer tubular member 12 to have different characteristics, and, in one presently preferred embodiment, the proximal section 13 is stiffer than the distal section 14.

A distensible balloon 17 is carried by outer tubular member 12 toward the distal end of the outer tubular member. In the embodiment illustrated, the balloon is formed as an integral part of the wall of the outer tubular member 12, but it can be formed separately, if desired, and secured to the exterior of the outer tubular member 12.

An axially extending lumen or passageway 19 is formed within inner tubular member 11, and an annular lumen or passageway 21 is formed between the inner tubular member 11 and the inner sidewall of the outer tubular member 12 on the proximal side of the balloon. Passageway 21 communicates with the interior of the balloon and provides means for inflating and deflating the balloon. On the distal side of the balloon, the inner and outer tubular members are sealed together by suitable means such as heat sealing or adhesive bonding to close the distal end of the balloon and passageway 21.

Perfusion holes 31 extend through the sidewalls of inner tubular member 11 and outer tubular member 12 and communicate with the passageway formed by luminal opening 19 on the distal side of the balloon. In the embodiment illustrated, these openings are arranged in longitudinally offset pairs on diametrically opposed sides of the tubular members.

On the proximal side of the balloon, the sidewalls of inner tubular member 11 and outer tubular member 12 are bonded together along one side thereof, as indicated at 32, for a distance on the order of 10-12 cm. In the embodiment illustrated, inner tubular member is positioned eccentrically of the outer tubular member in this limited region, and the confronting portions of the tubular members can be secured together by suitable means, such as heat sealing or adhesive bonding. The area in which the tubular members are bonded together is limited in circumferential extent as well as in length, and, even though the bonding is of sufficient extent to prevent leakage between openings 33 and outer passageway 21, it does not interfere appreciably with the flow of the inflation medium through passageway 21.

Perfusion holes 33 extend through the portions of the sidewalls of the tubular members 11 and 12 which are bonded together at 32 on the proximal side of the balloon 17. These openings communicate with the lumen 19 and together with perfusion holes 31 provide means by which blood can flow through the balloon when the balloon is inflated. Openings 33 extend for a distance on the order of 8-10 cm on the proximal side of the balloon.

Figure 2:
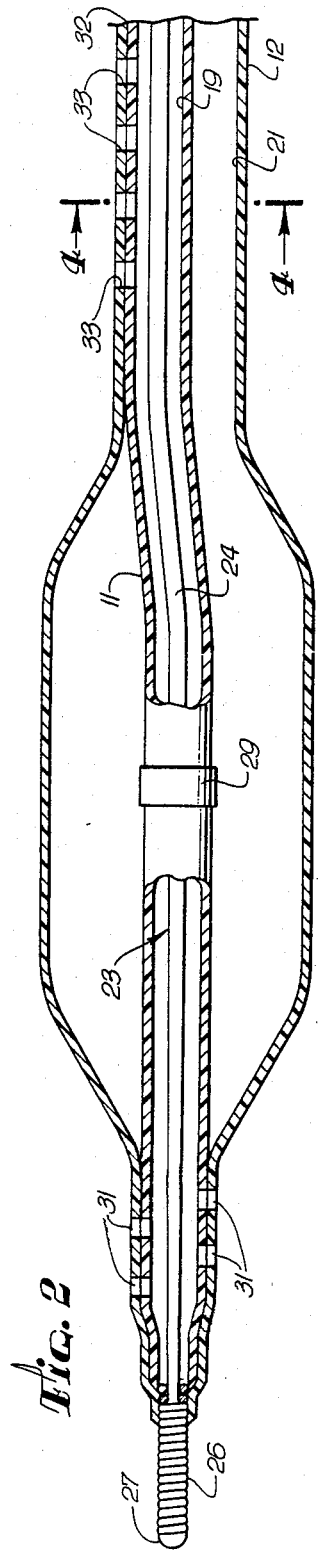
FIG. 2 is an enlarged fragmentary centerline sectional view of the embodiment shown in FIG. 1.
Figure 4:
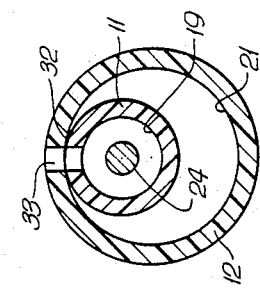
FIG. 4 is an enlarged cross-sectional view taken along line 4—4 of FIG. 2.
Figure 3:
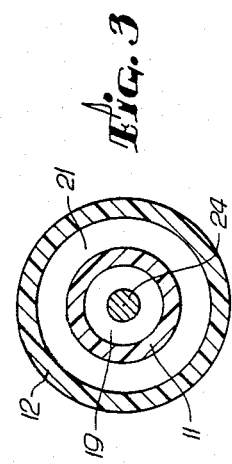
FIG. 3 is an enlarged cross-sectional view taken along line 3—3 of FIG. 1.

A guidewire 23 extends through the lumen 19 in inner tubular member 11, as shown in FIG. 2. The guidewire 23 comprises a shaft 24 having a diameter substantially smaller than the diameter of lumen 19 and a flexible tip portion 26 which extends beyond the distal ends of the tubular members 11 and 12. The tip portion comprises a flexible spring coil 26 which is soldered to the distal end portion of the wire shaft, with a rounded tip 27 at the distal end of the coil. The distal end portions of tubular members 11 and 12 are heat sealed or otherwise secured to the proximal end portion of the coil 26 to close the distal end of the passageway formed by lumen 19. In the embodiment illustrated, the distal end portions of the two tubular members 11 and 12 are shrunk down and heat sealed to the proximal end portion of the coil.

A fluoroscopically visible marker 29 comprising a band of radiopaque material is mounted on inner tubular member 11 inside the balloon. This marker is located midway between the ends of the balloon. The tip 27 and all or part of coil 26 may be made from radiopaque material such as platinum, tungsten, iridium, gold, rhenium, tantulum and alloys of these materials.

The proximal end of the catheter is provided with means for connecting the catheter to external devices such as a source of pressurized fluid (not shown) for inflating the balloon and a source of dye (not shown) for injection through the catheter 10. This means includes a first side arm adapter 36 having a port which communicates with the inflation/deflation passageway 21 and a second side arm adapter 37 which communicates with the inner passageway 19. A control knob 38 is affixed to the proximal end portion of guidewire 23 to facilitate rotation thereof to steer the catheter as it is introduced into the coronary anatomy of a patient.

In the use of the catheter of the invention, the catheter is introduced into the blood vessel of a patient such as the femoral artery through a guiding catheter and advanced beyond the guiding catheter to a desired location within the patient's cororary anatomy. The flexible tip portion 26 of the guidewire 23 can be pre-bent to a desired shape, and the catheter 10 can be steered as it is extended beyond the distal end of the guiding catheter by rotation of the guidewire knob 38. The catheter 10 is advanced in the patient's coronary vascularity until balloon 17 crosses the lesion to be treated. The balloon 17 is then inflated to compress the atherosclerosis and thereby reopen the artery and reestablish suitable blood flow therethrough. While the ballloon is inflated, blood can flow through the balloon through perfusion holes 31, 33, and lumen 19. With most lesions in the coronary arteries, one or more of the proximal perfusion holes 33 will be in the coronary ostium where blood flow is greater when the balloon is inflated.

The invention has a number of important features and advantages. The fixed guidwire permits the catheter to be steered through the tortuous passageways of the coronary arteries. the perfusion holes provide blood flow through the balloon when it is inflated, which allows the balloon to remain inflated for substantially longer periods of time than would otherwise be possible without danger to the heart muscle.

It is apparent from the foregoing that a new and improved dilatation catheter has been provided for use in coronary angioplasty. While the invention is described herein primarily in terms of a steerable dilatition catheter having a guidewire secured to the distal tip of the catheter, a separate guidwire could be used. As will be apparent to those familiar with the are, other improvements and modifications can be made without departing form the scope of the invention as defined by the following claims.

What is claimed is:

1. A steerable dilatation catheter for use in coronary angioplasty, comprising:
    (a) an outer tubular member having proximal and distal portions and having an inflatable balloon toward the distal end thereof;
    (b) an inner tubular member disposed within the outer tubular member having an inner lumen and proximal and distal portions and generally defining an annular passageway with the outer tubular member for inflation and deflation of the balloon, the distal portion of the inner tubular member extending through and beyond the interior of the balloon;
    (c) means sealing the sidewalls of the distal ends of the inner and outer tubular members together adjacent the distal end of the balloon to close the distal end thereof with at least one perfusion passageway passing through the sealed distal ends and being in fluid communication with the inner lumen of the inner tubular member;
    (d) means sealing the sidewalls of the inner and outer tubular members together at an eccentric location along one side thereof adjacent the proximal end of the balloon without substantial obstruction of the inflation/deflation passageway
    with at least one perfusion passageway extending through the sealed sidewalls of the inner and outer tubular members. said passageways being in fluid communication with the inner lumen of the inner tubular member for carrying blood therethrough to the perfusion passageways passing through the sealed sidewalls of the distal ends of the inner and outer tubular members; and
    (e) a guidewire extending through and fixed within the innez lumen in the inner tubular member with a distal portion of the guidewire extending beyond the distal end of the tubular members.

2. The steerable dilatation catheter of claim 1 wherein the inflatable balloon is formed as an integral part of the outer tubular member.

3. The steerable dilatation catheter of claim 1 wherein the proximal section of the outer tubular member is stiffer than the distal section thereof.

4. The steerable dilatation catheter of claim 1 wherein the guidewire comprises a shaft which extends through the inner tubular member with the tip portion of the guidewire extending beyond the distal end of the tubular members.

5. The steerable dilatation catheter of claim 4 wherein the distal tip of the guidewire is provided with a flexible wire coil.

* * * * *